(12) United States Patent
Wang et al.

(10) Patent No.: US 9,895,112 B2
(45) Date of Patent: Feb. 20, 2018

(54) CANCEROUS LESION IDENTIFYING METHOD VIA HYPER-SPECTRAL IMAGING TECHNIQUE

(71) Applicant: National Chung Cheng University, Chiayi County (TW)

(72) Inventors: Hsiang-Chen Wang, Chiayi County (TW); Shin-Hua Chen, Chiayi County (TW); Shih-Wei Huang, Chiayi County (TW); Chiu-Jung Lai, Chiayi County (TW); Chu-Chi Ting, Chiayi County (TW)

(73) Assignee: National Chung Cheng University, Chiayi County (TW)

( * ) Notice: Subject to any disclaimer, the term of this patent is extended or adjusted under 35 U.S.C. 154(b) by 113 days.

(21) Appl. No.: 15/146,123

(22) Filed: May 4, 2016

(65) Prior Publication Data
US 2017/0319147 A1   Nov. 9, 2017

(51) Int. Cl.
| | | |
|---|---|---|
| *G06K 9/52* | (2006.01) | |
| *A61B 5/00* | (2006.01) | |
| *G06T 7/00* | (2017.01) | |
| *G06T 7/60* | (2017.01) | |

(52) U.S. Cl.
CPC .......... *A61B 5/7282* (2013.01); *A61B 5/0075* (2013.01); *A61B 5/0084* (2013.01); *G06K 9/52* (2013.01); *G06T 7/0012* (2013.01); *G06T 7/60* (2013.01); *G06T 2207/30096* (2013.01)

(58) Field of Classification Search
CPC ... A61B 5/7282; A61B 5/0084; A61B 5/0075; G06T 7/60; G06T 7/0012; G06T 2207/30096; G06K 9/52
See application file for complete search history.

(56) References Cited

U.S. PATENT DOCUMENTS

| | | | |
|---|---|---|---|
| 6,258,576 B1 * | 7/2001 | Richards-Kortum | A61B 5/0059 425/288 |
| 7,515,952 B2 * | 4/2009 | Balas | A61B 1/303 359/362 |
| 2008/0267472 A1 * | 10/2008 | Demos | A61B 1/00009 382/128 |

* cited by examiner

*Primary Examiner* — Siamak Harandi
(74) *Attorney, Agent, or Firm* — Fishman & Associates, LLC.

(57) ABSTRACT

A cancerous lesion identifying method via hyper-spectral imaging technique comprises steps of: acquiring a plurality of first pathology images via an endoscopy, wherein the first pathology images are cancerous lesion images respectively; importing the first pathology images into an image processing module to acquire a plurality of first simulating spectra of the first pathology images so as to generate a principle component score diagram in accordance with the first simulating spectra; defining a plurality of triangle areas in the principle component score diagram in accordance with the first simulating spectra; determining whether a principle component score of a second simulating spectrum of a second pathology image is within any one of the triangle areas; and confirming the second pathology image belongs to one of the cancerous lesion images when the principle component score of the second simulating spectrum is within any one of the triangle areas.

8 Claims, 21 Drawing Sheets

|  | ORIGINAL | | | | SIMULATING | | | | COLOR DIFFERENCE |
|---|---|---|---|---|---|---|---|---|---|
|  | L | a | b | | L | a | b | | |
| 1 | 50.09843 | 19.08707 | 20.64912 | | 50.09843 | 20.96076 | 17.93277 | | 2.594541 |
| 2 | 83.70418 | 19.1865 | 14.8633 | | 83.70418 | 16.28975 | 14.928 | | 2.042296 |
| 3 | 69.81877 | -7.74034 | -25.9512 | | 69.81877 | -8.93241 | -26.456 | | 0.899792 |
| 4 | 59.97531 | -13.6012 | 12.92233 | | 59.97531 | -17.0098 | 14.78451 | | 2.320287 |
| 5 | 72.24725 | 5.957376 | -27.5122 | | 72.24725 | 3.88018 | -23.8898 | | 1.436135 |
| 6 | 81.56532 | -33.7691 | -5.9428 | | 81.56532 | -25.9006 | -2.48419 | | 3.924307 |
| 7 | 67.57656 | 30.56204 | 42.16302 | | 67.57656 | 32.57781 | 36.55611 | | 3.541775 |
| 8 | 60.51991 | 4.838911 | -48.0758 | | 60.51991 | 8.860095 | -64.3344 | | 3.539966 |
| 9 | 50.64061 | 36.30945 | 10.43552 | | 50.64061 | 37.8666 | 13.70207 | | 1.884724 |
| 10 | 26.87364 | 6.289957 | -12.5182 | | 26.87364 | 14.09477 | -6.06222 | | 9.353387 |
| 11 | 75.07243 | -22.3148 | 41.26876 | | 75.07243 | -22.9269 | 37.08563 | | 1.861902 |
| 12 | 74.5717 | 16.58428 | 52.28235 | | 74.5717 | 20.54623 | 46.22905 | | 4.189262 |
| 13 | 57.00707 | 2.790768 | -51.7897 | | 57.00707 | 7.957496 | -81.5339 | | 6.024069 |
| 14 | 67.57488 | -37.26 | 20.71825 | | 67.57488 | -47.5667 | 19.19687 | | 4.137267 |
| 15 | 47.76556 | 38.12681 | 15.90608 | | 47.76556 | 38.25811 | 16.01495 | | 0.065263 |
| 16 | 90.71209 | 4.142883 | 67.62919 | | 90.71209 | 2.188009 | 71.53724 | | 1.601011 |
| 17 | 66.94201 | 45.01134 | -13.5783 | | 66.94201 | 45.24169 | -11.0441 | | 1.250559 |
| 18 | 71.85582 | -27.0286 | -35.24 | | 71.85582 | -23.6254 | -30.184 | | 2.124939 |
| 19 | 96.37304 | 0.011366 | 0.658302 | | 96.37304 | -1.53344 | -2.62034 | | 3.768381 |
| 20 | 88.26455 | -0.64205 | -2.31098 | | 88.26455 | 0.035317 | 1.075784 | | 3.404654 |
| 21 | 81.20468 | -1.65044 | -3.32447 | | 81.20468 | -0.7369 | -2.19019 | | 1.558863 |
| 22 | 59.33575 | -2.00762 | -3.85241 | | 59.33575 | -0.52156 | -0.58618 | | 3.497847 |
| 23 | 37.74099 | -2.34951 | -3.4925 | | 37.74099 | -2.05863 | 3.88569 | | 6.872186 |
| 24 | 20.76816 | -2.96673 | -3.29706 | | 20.76816 | -4.16671 | 0.152327 | | 3.559357 |
|  |  |  |  | | | | | AVERAGE | 3.143865 |

FIG. 3

CANCEROUS LESION IDENTIFYING METHOD VIA HYPER-SPECTRAL IMAGING TECHNIQUE

BACKGROUND OF THE INVENTION

1. Field of the Invention

The present invention relates to a cancerous lesion identifying method, and more particularly to a cancerous lesion identifying method by implementing hyper-spectral imaging technique and principle component analysis.

2. Description of Related Art

With the development of hyper-spectral imaging technique is well developed, the hyper-spectral imaging technique has been implemented in medical examination, such as early stage oral cancer detection, oral lesions detection of enterovirus, rectal mucosa detection, and so on. Different equipments adopt different kinds of hyper-spectral imaging techniques. Accordingly, one of the conventional hyper-spectral imaging systems is to implement a single point spectrum analyzer with a two-dimensional scanning system. This kind of hyper-spectral imaging system can get best simulating spectrum and spatial resolution, but it is time consuming to read data. Another conventional hyper-spectral imaging system is to implement digital cameras with liquid crystal tunable filters and microscopes, and is used in bone marrow cells detection. This method can separate materials from the bone marrow cells, but the reading speed of the spectrum data is limited by the effect of the liquid crystal tunable filters. Moreover, another one of the hyper-spectral imaging systems is to implement hyper-spectral cameras to perform spectrum and image analysis and has been used in cosmetic and skin detection. This hyper-spectral imaging system has a very high image resolution, but it needs to process huge data and the cost is higher.

Partial test and diagnosis from the endoscopy at an early stage is a key point to reduce mortality rate. The conventional medical treatment detects the esophageal lesions at the early stage by a white light endoscopy technique. The white light endoscopy detection includes three characteristic variations in accordance with the early stage esophageal mucosa: (1) Mucosa color variation with red and white types. The red variations are red regions with clear edges and the mucosa looks rough and muddy. A few of red variations are large red regions with unclear edges. The white variations are mucosa white spots, which are dispersed, have clear boundaries and unequal sizes, and are rough, dull and slightly bumpy. (2) Mucosa becomes thickened and blood vessel structure varies. The skin on the normal esophageal mucosa is translucent and blood vessels under the mucosa are visible. When the skin on the mucosa has cancer lesions, the blood vessels under the mucosa are not transparent. (3) Morphology of the mucosa changes, such as erosion, plaque, roughness, nodule or any combinations thereof. The three aforementioned morphological changes will make the esophageal mucosa lose its normal structure and color. However, when using the conventional white light endoscopy, the detailed structure of the esophageal endoscopy may not be observed clearly, and biopsy and staining techniques are required for diagnosis. The detection method of the chromoendoscopy is to enhance the color contrast between the lesioned and normal mucosas by orally taking, injecting, spraying the agent directly so as to make the color contrast between the lesioned and normal mucosa more clear. So, the chromoendoscopy can help the cancerous lesions identification and the targeted biopsy, and accuracy of the diagnosis of the early stage esophageal lesions can be enhanced. The chromoendoscopy includes the following manners. For example, iodine staining, since the esophageal mucosa is squamous cell epithelium, many glycogens are included within the cells and glycogen has a strong affinity with iodine solution and will be stained brown. On the contrary, when the pathological lesion of the mucosa occurs, cells with glycogen will reduce or disappear and it is not easy to stain mucosa brown with iodine solution. Accordingly, when performing endoscopy, the iodine solution may be sprayed on the surface of the esophageal. If the area of the esophagus cannot be stained brown by the iodine solution, the probability of early esophageal cancer is highly suspected. The iodine staining is one of the most common chromoendoscopies. Toluidine blue staining implements an eosinophilic dye, which has affinity to DNA and RNA in cancer cells and precancerous cells, so Toluidine blue can be used to detect pathological lesions or cancerous lesions. The toluidine blue staining is processed with an absorbent agent. The normal esophageal squamous cells may not absorb toluidine blue and cannot be stained, but intestinal cells and cone cells may absorb toluidine blue and are stained blue. Therefore, the toluinine blue staining is usually used in the detection of esophageal adenocarcinoma. However, according to medical literature, the toluidine blue may cause the damage of the DNA and the toluidine blue staining is time consuming and relied on the operator's experience. Acetic acid staining may cause cytoplasmic proteins within the cell to have reversible changes. The acetic acid staining is normally used at a concentration of 1.5% to 3%. After 2 to 3 minutes spraying, the esophageal squamous mucosa still shows white color but the esophageal columnar epithelium turns red so as to recognize the remaining cone cells. Because of the uneven dye concentration, the improper spraying method or the limitation of the agent, staining difference may occur at the pathological lesions, and the positioning may not be accurate or lesions may be missed. Accordingly, single staining is limited and double staining may be used to resolve these limitations.

Except for the aforementioned chemical chromoendoscopy, there is electronic endoscopy technique, such as Narrow Band Imaging (NBI) or Fujinon Intelligent Chromoendoscopy (FICE). Both of the methods are based on selecting a certain wavelength spectrum. The NBI implements the bandwidth of the narrow spectrum of the filter. The FICE is to divide the conventional white color into many spectroscopic images each with a single signal wavelength and some of the spectroscopic images with the proper wavelengths are selected to be combined.

Since the choromoendoscopy detection is very difficult, the medical literature provides two sensitive and convenient clinic methods to identify benign or malignant lesions: Multiphoton Microscopy (MPM) and Surface-enhanced Raman Scattering (SERS) with polymer nonoparticles, which are also used in cancerous cells detection because of the advancement in Biology. By the signals in Two-Photon Excited Fluorescence (TPEF) and Second Harmonic Generation (SHG) in MPM, the esophageal lesions can be identified by the difference of the background signal and autologous fluorescent. As shown in FIG. 13, according to the comparison of the signal strength between SHG and TPEF, the signal strength of the cancerous tissues is obviously lower than the normal tissues thereof. It is to be understood that collagen content, distribution and morphology may be changed because cancer cells occupy submucosal tissues. Therefore, the signal strength ratio can be used as an indicator to distinguish normal, precancerous normal, precancerous change and cancerous tissues of the esophagus. On the other hand, Raman spectra can provide specific fingerprint formation information in molecular composition and biological structure, and those optical techniques can be used to diagnose and determine cancer. However, the normal Raman spectra technique has two significant drawbacks: background fluorescence interference is too strong and the efficiency of the Raman scattering is too low. Therefore, the difficulties in actual clinic practice occur. SERS can provide a solution for those questions and the weak Raman signal can be strengthened to $10^{14}$ times. Since the fluorescent signal at the background will be absorbed by the molecules on the metal surface of the nano particles, the fluorescent signal will be significantly decreased as shown in FIG. 14. When the nano silver particles are not dropped into the sample of the esophageal lesion tissues, the Raman signal is very weak as the waveform of the Raman spectra in FIG. 14. After two minutes since the nano silver particles with 25 nm diameters are dropped into the esophageal lesion tissues, the strength of the Raman signal is significantly increased after measuring, as the surface strength Raman spectra waveform in FIG. 14. Finally, as the results shown in FIG. 15, the surface-enhanced Raman spectroscopy signals in the normal tissue waveform and the cancerous lesion tissue are compared to distinguish the waveform with spectrum difference.

However, early stage lesions are not obvious under the white light detection, and the lesions are easy to be ignored and the treatment is delayed. Since the endoscopy technique is well developed in recently years, the endoscopy working with some of the chemical and optical principles can enhance the tiny esophageal lesions to increase the diagnosis rate of the early cancerous lesions, such as Lugol's chromoendoscopy and NBI endoscopy. However, the Lugol's chromoendoscopy will spray dye to have development results, but the dye is not evenly distributed, causing the difficulty of the determination. In addition, the dye may make the patient's chest feel uncomfortable such as tingling or burning. NBI will involve certain subjectivity in analysis of images and is affected by some factors. For example, when the lesions, such as blending or inflammation, occur, the vision is fuzzy and the resolution of the images is poor. If the patient has some other significant organ dysfunctions, such as heart disease, lung disease or unstable conditions, the condition and the function of the organ have to be evaluated carefully to determine if the patient is suitable to do the test. In the detection of the esophageal cancer, the NBI is the current mainstream technology without spraying dye to include optical dye effect and the operation thereof is very easy. Only one button is to push to switch between the white light mode and the NBI mode so as to repeatedly observe. However, the detection is based on observing surface vessels, such as the changes in Intra-epithelial Papillary Capillary Loop (IPCL), much relying on the subjective determination of the clinicians.

According to the working theory of the aforementioned NBI, the blue light and the green light with two narrow frequencies (415 nm and 540 nm) respectively are filtered by Xenon with a specific filter. Angiogenesis occurs on the mucosal surface at the early stage of the esophageal cancer, and the passing-through depth of the visible light is deeper when the wavelength of the visible light is longer. Therefore, the red light is abandoned and only the blue light and the green light are considered. The Charge-coupled device (CCD) will receive the reflective light of the mucosa emitted by the blue light and the green light with narrow frequencies. The reflective light is converted to digital signals and the digital signals are divided into three channels (R, G, B) by a color reorganization manner in accordance with human color vision sensitivity. The blue light (415 nm) is distributed to B and G channels and the green light (540 nm) is distributed to R channel Finally, the endoscopy with the blue light and the green light may display color image by a color image processing. The aforementioned method may sharpen the image of the tiny blood vessels on the mucosal surface and strengthen the contrast. If the magnification of the endoscopy is implemented, the lesions may be magnified more than 80 times. Therefore, the clinicians may clearly observe the lines, the arrangement and the size variation of the veins on the surface of the lesions. Therefore, by observing the differences of the areas of the brown lesions, the diagnosis rate of the early stage esophageal cancer may be efficiently increased.

Principle component analysis is a common method in multivariate statistics and people have used the principle component analysis in color technique since 1960. The idea of the principle component analysis is to find a subspace with the data set having multiple variables, and the subspace may keep data variation and the number of the principle components is less than the number of original variables. The original data is projected into the subspace to perform an analysis. The main purposes of the principle component analysis are: (1) to define a large amount of spectrum information in a spindle direction and (2) to simplify the information data. After resetting the original data, highly correlated and mutually independent variables are calculated and the variables are analyzed to get the principle components. The variations in most of the data within the original information may be explained. The example in FIG. 16 is used to explain the geometric meaning of the principle component analysis. There are two groups of uneven data points in FIG. 16, in view from X1 and Y1 coordinates, and it is hard to separate those two groups of data from X1 and Y1 coordinates. The data from X1 and Y1 coordinates has no obvious boundaries. After calculating by the principle component analysis, a spindle direction is obtained as X2 shown in FIG. 16. Therefore, the data is projected on the X2 and all of the data includes a new coordinate value X2. Obviously, the data on the X2 may be obviously distinguished. Accordingly, these are the characteristics of the principle component analysis.

Therefore, if the hyper-spectral imaging technique can work with the principle component analysis, a new optical detection method may be provided. The clinicians may quickly identify the esophageal lesions at the early stage by comparing the results of the principle component analysis diagram and checking the tendency of the spectra characteristics for IPCL type variation of the esophageal cancer lesions in the NBI endoscopy images, and the spectra characteristics of the normal tissues, precancerous lesions and cancerous lesions of the esophagus in the white light and iodine endoscopy.

SUMMARY OF THE INVENTION

Accordingly, an objective of the present invention is to provide a cancerous lesion identifying method via hyper-spectral imaging technique to quickly evaluate the probabilities of cancer at various stages.

According to the aforementioned objective, a cancerous lesion identifying method via hyper-spectral imaging technique comprises steps of: acquiring a plurality of first pathology images via an endoscopy, wherein the first pathology images are cancerous lesion images respectively;

importing the first pathology images into an image processing module to acquire a plurality of first simulating spectra of the first pathology images so as to generate a principle component score diagram in accordance with the first simulating spectra; defining a plurality of triangle areas in the principle component score diagram in accordance with the first simulating spectra; determining whether a principle component score of a second simulating spectrum of a second pathology image is within any one of the triangle areas; and confirming the second pathology image belongs to one of the cancerous lesion images when the principle component score of the second simulating spectrum is within any one of the triangle areas.

By the cancerous lesion identifying method via the hyper-spectral imaging technique in the present invention, the cancerous lesion images are digitized and the diagnosis rate of the clinicians may be efficiently increased to help the patients to start the treatments as soon as possible.

BRIEF DESCRIPTION OF THE DRAWINGS

FIG. 3 is a table for 24 mini color checkers;

DETAILED DESCRIPTION OF THE PREFERRED EMBODIMENT

Figure 1:
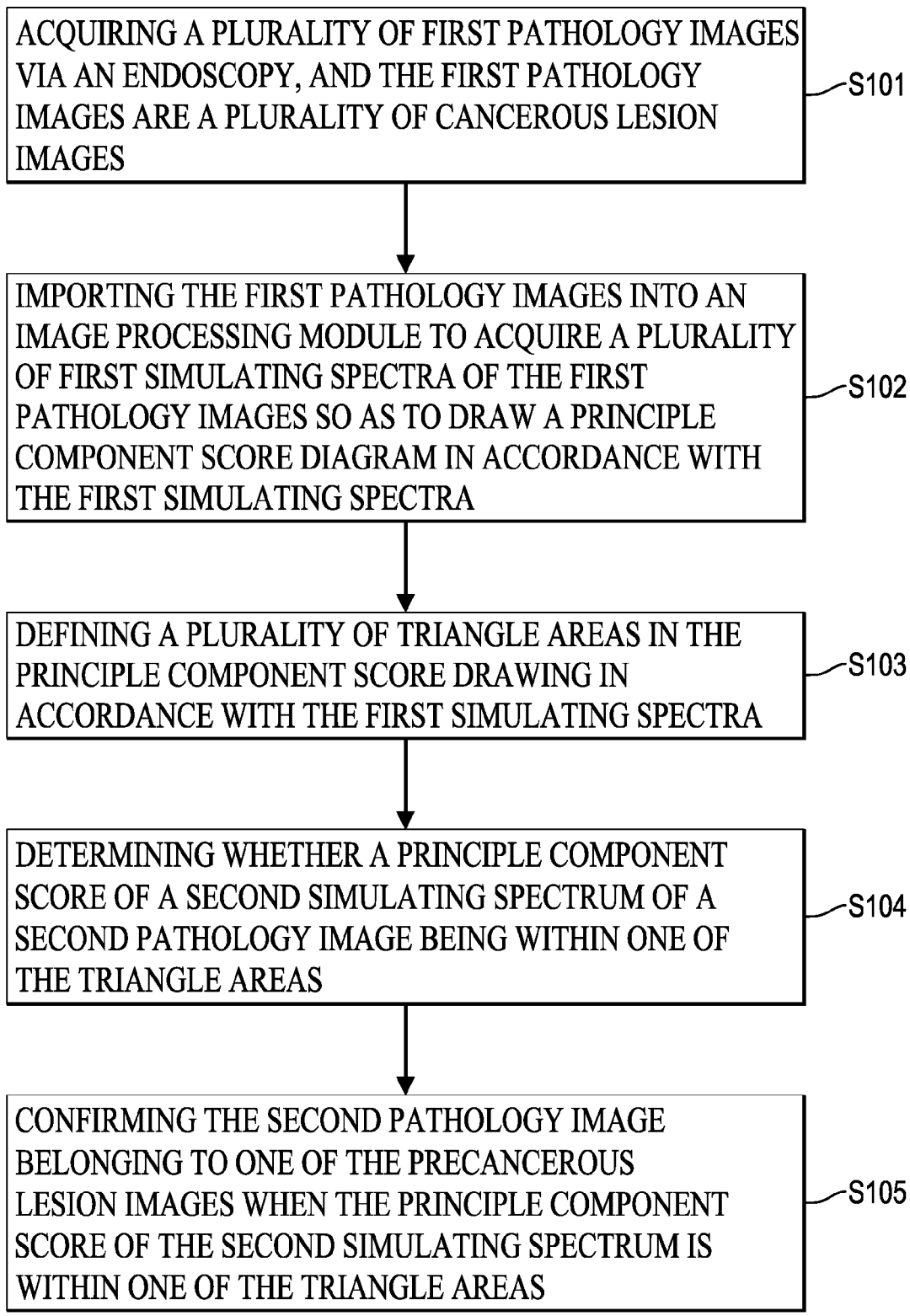
FIG. 1 is a flow chart of a cancerous lesion identifying method via hyper-spectral imaging technique in an embodiment of the present invention.
Figure 2A:
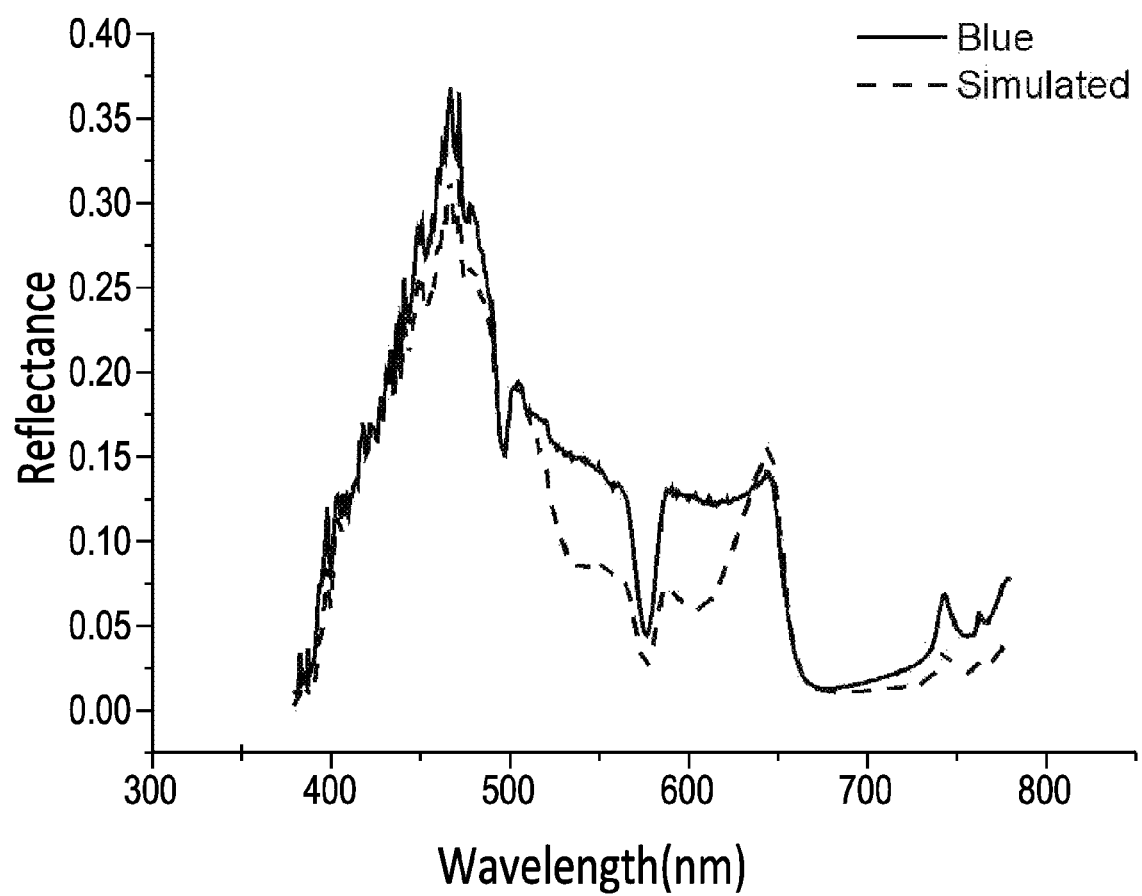
FIG. 2A-FIG. 2F are waveforms diagrams of comparisons between stimulation spectra and practical measuring spectra for the 24 mini color checkers.
Figure 2B:
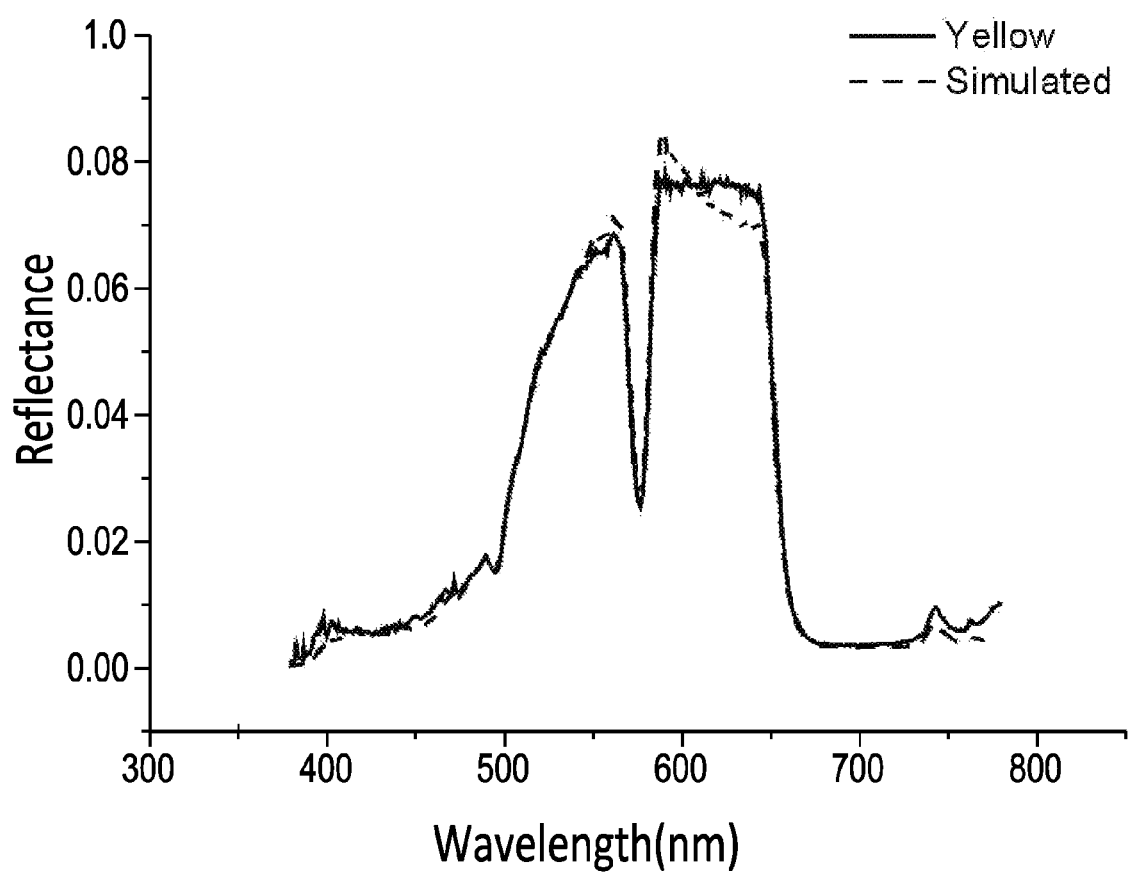
Figure 2C:
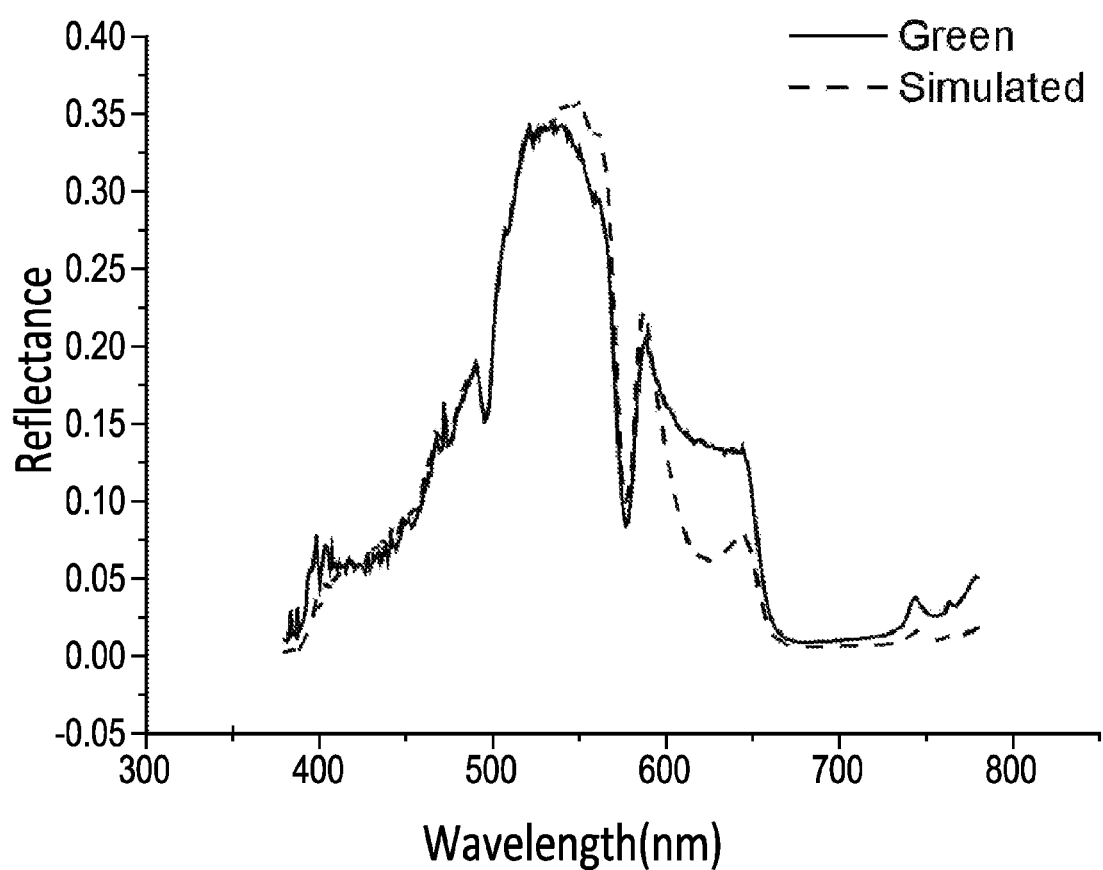
Figure 2D:
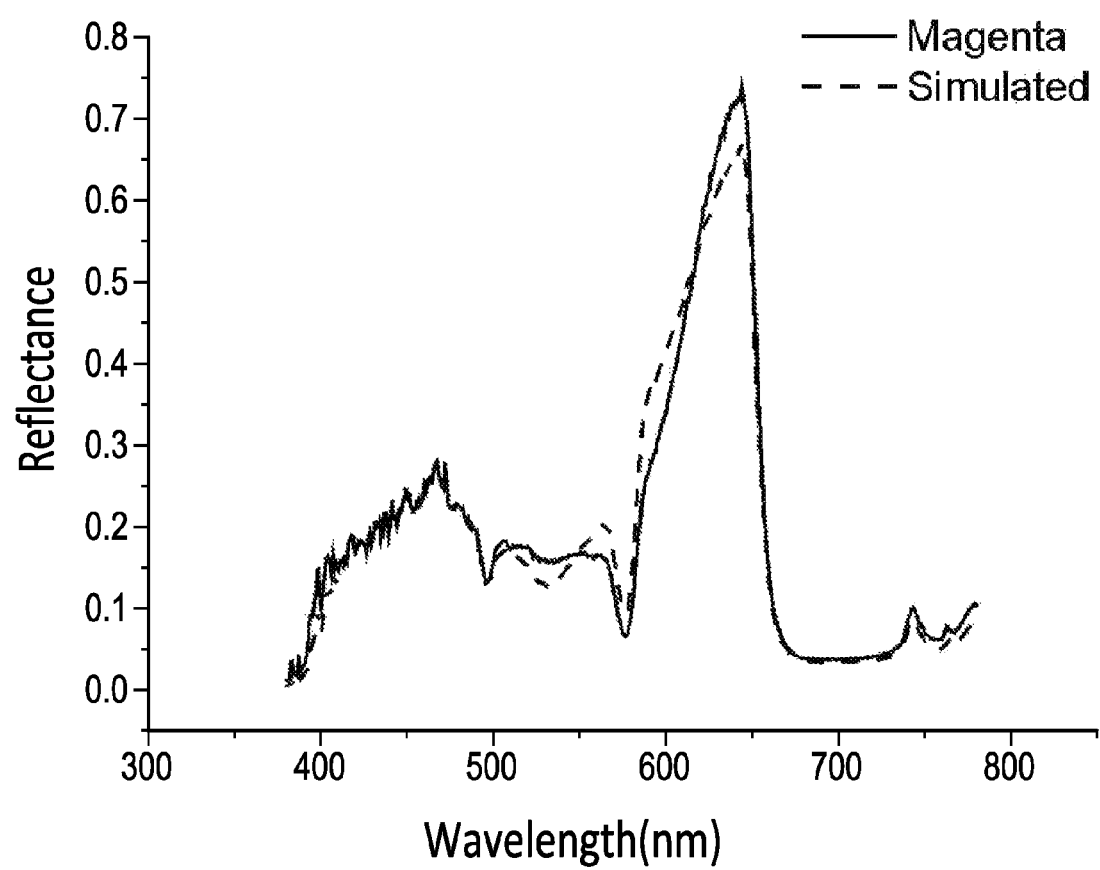
Figure 2E:
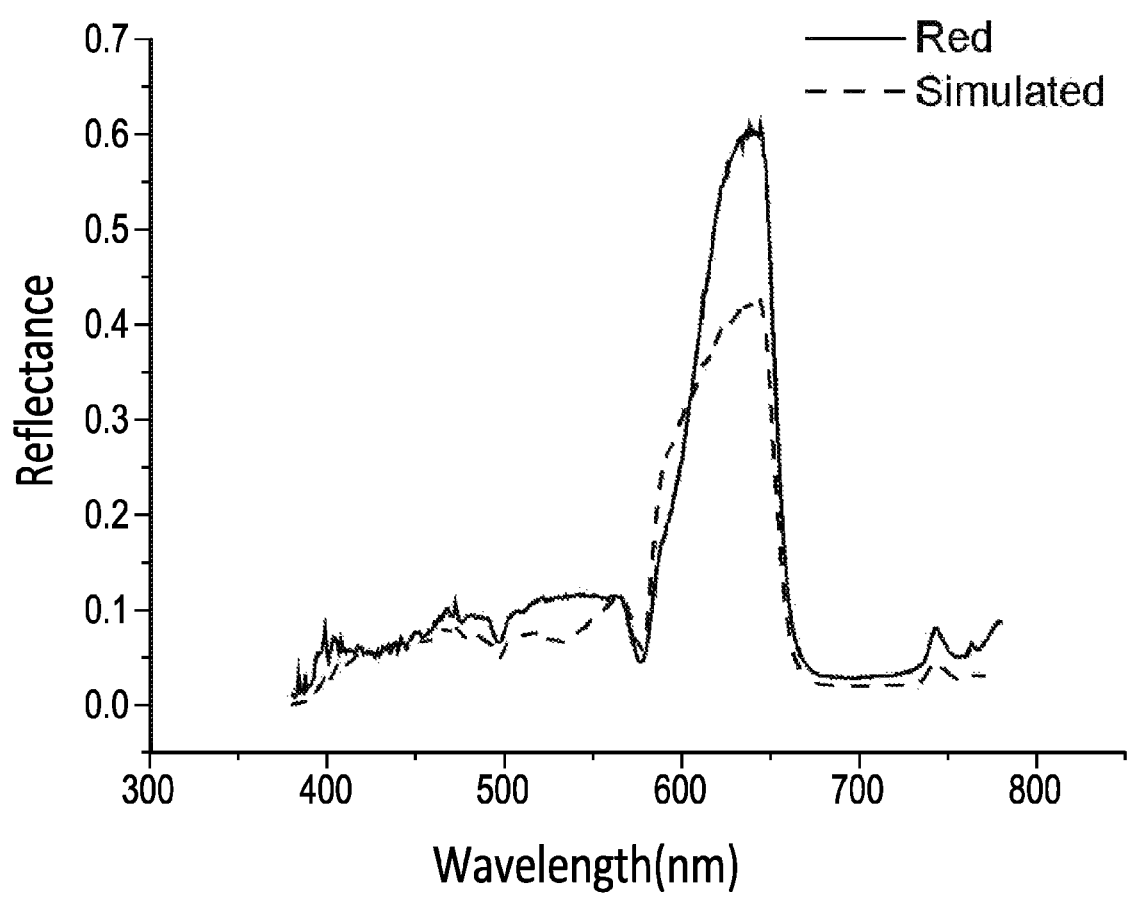
Figure 2F:
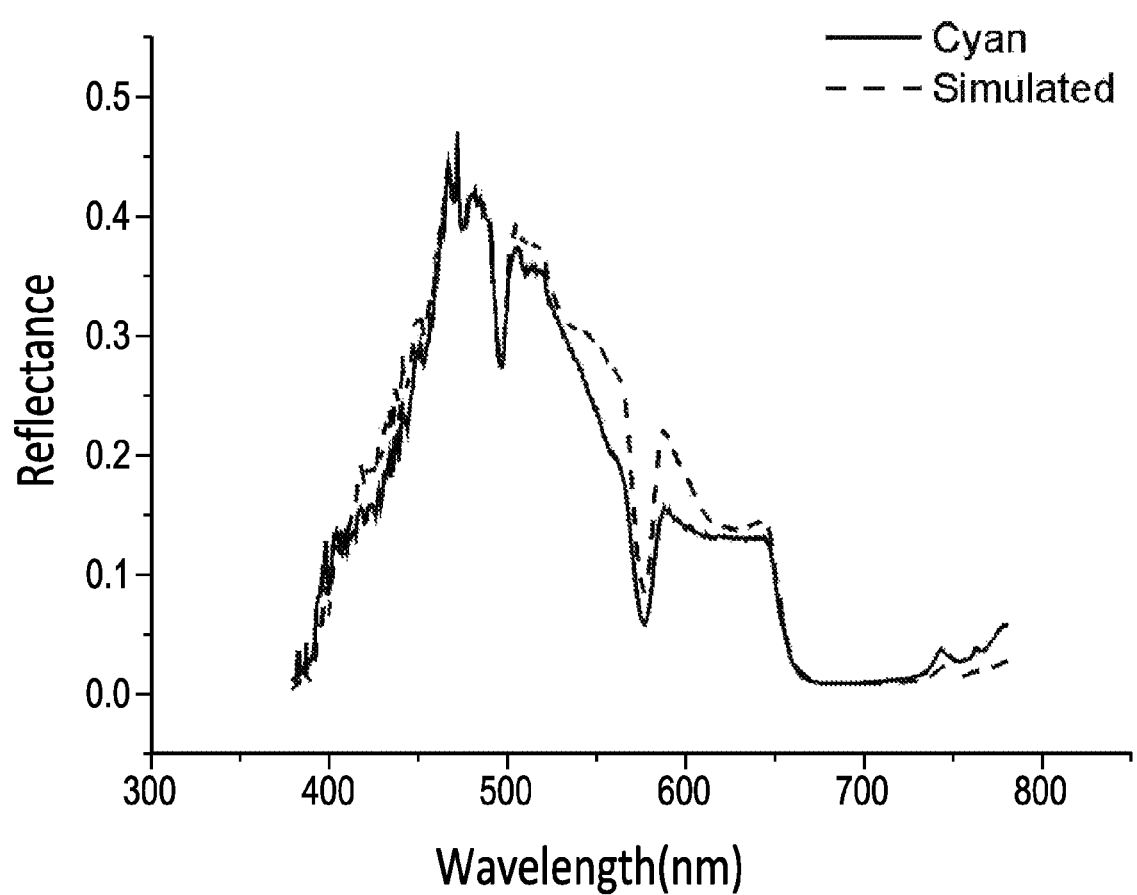

FIG. 1 is a flow chart of a cancerous lesion identifying method via hyper-spectral imaging technique in an embodiment of the present invention. As shown in FIG. 1, in step S101, a plurality of first pathology images are acquired via an endoscopy and the first pathology images are cancerous lesion images. The hyper-spectral imaging system is built within the endoscopy and a high resolution spectrometer. The hyper-spectral imaging system can acquire image information of 24 mini color checkers. In order to determine cancerous lesions, the spectra at each of the pixels in each of the first pathology images may be acquired and a relationship matrix between the spectrometer and the endoscopy has to be found first. The spectra of the 24 mini color checkers are measured by the spectrometer under the environment of the endoscopy. The range of the spectra is set at the wave band of visible light (380 nm-780 nm). For analytical purposes, each column of the matrix is the corresponding strength value of the wavelength and each row is the number of the mini color checkers.

The 24 color mini color checkers are filmed under the environment of the endoscopy. The output format of the 24 color mini checkers is sRGB (JPEG image data). By the calculation of the computer, Red (R) value, Green (G) value and Blue (B) value (0-255) at each of the mini color checkers can be obtained and are converted into $R_{srgb}$, $G_{srgb}$, and $B_{srgb}$ with smaller range (0-1). By the following equations, those RPG values are converted into tristimulus values X, Y, and Z under International Commission on Illumination (CIE) standard. The equations are:

$$\begin{bmatrix} X \\ Y \\ Z \end{bmatrix} = [T] \begin{bmatrix} f(R_{srgb}) \\ f(G_{srgb}) \\ f(B_{srgb}) \end{bmatrix} \quad (1)$$

where $$[T] = \begin{bmatrix} 0.4104 & 0.3576 & 0.1805 \\ 0.2126 & 0.7152 & 0.0722 \\ 0.0193 & 0.1192 & 0.9505 \end{bmatrix} \quad (2)$$

$$f(n) = \begin{cases} \left(\dfrac{n+0.055}{1.055}\right)^{2.2}, & n > 0.04045 \\ \left(\dfrac{n}{12.92}\right), & \text{otherwise} \end{cases} \quad (3)$$

Standard white is a reference white light of D65 light source at the s(standard)RGB and D65 light source is a most common artificial sunlight, and the D65 light source and the light source of the endoscopy measured by the spectrometer are different reference white lights. Therefore, those RGB values are required to perform correction by color adaption. In order to precisely calculate spectra values of the mini color checkers, the correction of the endoscopy is necessary. Similarly, the spectra measured by the spectrometer are converted into the tristimulus values X, Y, and Z under the CIE standard by the following equations (4)-(7) and $S(\lambda)$ is light source spectra of the endoscopy, $R(\lambda)$ is the spectrum value for each of the mini color checkers and $\bar{x}(\lambda)$, $\bar{y}(\lambda)$, and $\bar{z}(\lambda)$ are color matching functions.

$$X = k \int_{380nm}^{780nm} S(\lambda) R(\lambda) \bar{x}(\lambda) d\lambda \quad (4)$$

$$Y = k \int_{380nm}^{780nm} S(\lambda) R(\lambda) \bar{y}(\lambda) d\lambda \quad (5)$$

$$Z = k \int_{380nm}^{780nm} S(\lambda) R(\lambda) \bar{z}(\lambda) d\lambda \quad (6)$$

where $$k = 100 \bigg/ \int_{380nm}^{780nm} S(\lambda) \bar{y}(\lambda) d\lambda \quad (7)$$

The 24 mini color checkers are converted into XYZ values by the equations (4) to (7). By the conversion of the color adaption, new XYZ values can be obtained and the XYZ values are converted back to the RGB values. Then, the RGB values are set into the matrix [A]. The conversion relationship between the spectrometer and the endoscopy can be found by three-order polynomial regression of the RGB values. The three-order polynomial regression of the matrix is:

$$[C]=[A]\text{pinv}[B] \quad (8)$$

where $$[B]=[1,R,G,B,RG,GB,BR,R^2,G^2,B^2,RGB,R^3,G^3,B^3,\\RG^2,RB^2,GR^2,GB^2,BR^2,BG^2]^T \quad (9)$$

"R", "G", "B" are the corresponding RGB values at each of the mini color checkers filmed by the endoscopy. The RGB correlation of the mini color checkers are converted into the tristimulus value XYZ under the CIE standard and are set to be [β]. Finally, the conversion matrix [M] of the endoscopy and the spectrometer can be obtained by:

$$[M]=[\alpha]\text{pinv}[\beta] \quad (10)$$

Each of the pixels at the first pathology image filmed by the endoscopy times the RGB values to obtain the linear regression [C] and is calculated by the equations (1) to (3) to obtain the corresponding XYZ value. The spectra for each of the mini color checkers (wave band 380 nm to 780 nm) are measured by the following equation:

$$[Spectra]_{380-780nm} = [E][M]\begin{bmatrix}X\\Y\\Z\end{bmatrix} \quad (11)$$

In this step, the spectrometer measures spectra reflected from or penetrated by an object. The spectra are inputted into the equation (11) to calculate colors. Each of the pixels in one piece of the picture can perform color image recovering by the equation (11). The color image is calculated by the stimulated spectrometer measurement.

Therefore, a comparison between stimulation spectra and practical measuring spectra for the 24 mini color checkers are shown in FIG. 2A to FIG. 2F. In addition, in order to verify the feasibility of color reproduction, the actual color and the 24 mini color checkers filmed by the endoscopy and the stimulated color of the 24 mini color checkers perform color different calculation by a color different equation. The color different calculation procedure is as the following.

Firstly, the tristimulus XYZ values measured by the endoscopy and the spectrometer are converted into chromatic coordinates (L*, a*, b*) under the CIE 1976 standard, where:

$$L^* = 116 f\left(\frac{Y}{Y_n}\right) - 16 \quad (12)$$

$$a^* = 500\left[f\left(\frac{X}{X_n}\right) - f\left(\frac{Y}{Y_n}\right)\right] \quad (13)$$

$$b^* = 200\left[f\left(\frac{Y}{Y_n}\right) - f\left(\frac{Z}{Z_n}\right)\right] \quad (14)$$

$$f(n) = n^{\frac{1}{3}}, \text{ for } n > 0.008856 \quad (15)$$
otherwise $f(n) = 7.787n + 0.137931$ Thereafter, Euclidean distance between two points at the chromatic coordinates under the CIE 1976 standard is the color difference of the two points:

$$\Delta E_{ab}^* = \sqrt{(\Delta L^*)^2 + (\Delta a^*)^2 + (\Delta b^*)^2} \quad (16)$$

Each of the color difference values of the 24 mini color checkers can be calculated by the aforementioned equations. The average color difference value is about 3.14 as shown in FIG. 3. Normally, when the color difference value is smaller than 4, the difference is hard to be determined by human eyes. The result in FIG. 3 shows the aforementioned equations can perform color reproduction precisely and can be used in color performance for any images.

In step S102, the first pathology images are imported into an image processing module to obtain a plurality of first stimulating spectra of the first pathology images. The image processing module is made of a computer installed with software having functions of hyper-spectral imaging processing. The software having function of hyper-spectral imaging processing can be developed by program design software, such as Microsoft Visual Basic and so on.

In accordance with histopathology, the white light images and the iodine staining images are divided into four different types: Normal, Dysplasia, between Dysplasia and Esophageal Cancer (ECA), and ECA. The cells abnormally grow or develop to be cancerous cells are called Dysplasia. The NBI enlarged images are divided into four types: Intraepithelial papillary capillary loop type 4 (IPCL-IV severe Dysplasia), IPCL type 5-1 (IPCL V1 Severe Dysplasia), IPCL type 5-1, IPCL-V1 Squamous Cell Carcinoma (SCC) (IPCL-V1 SCC), and IPCL type 5-3 (IPCL-V3 SCC).

Figure 4:
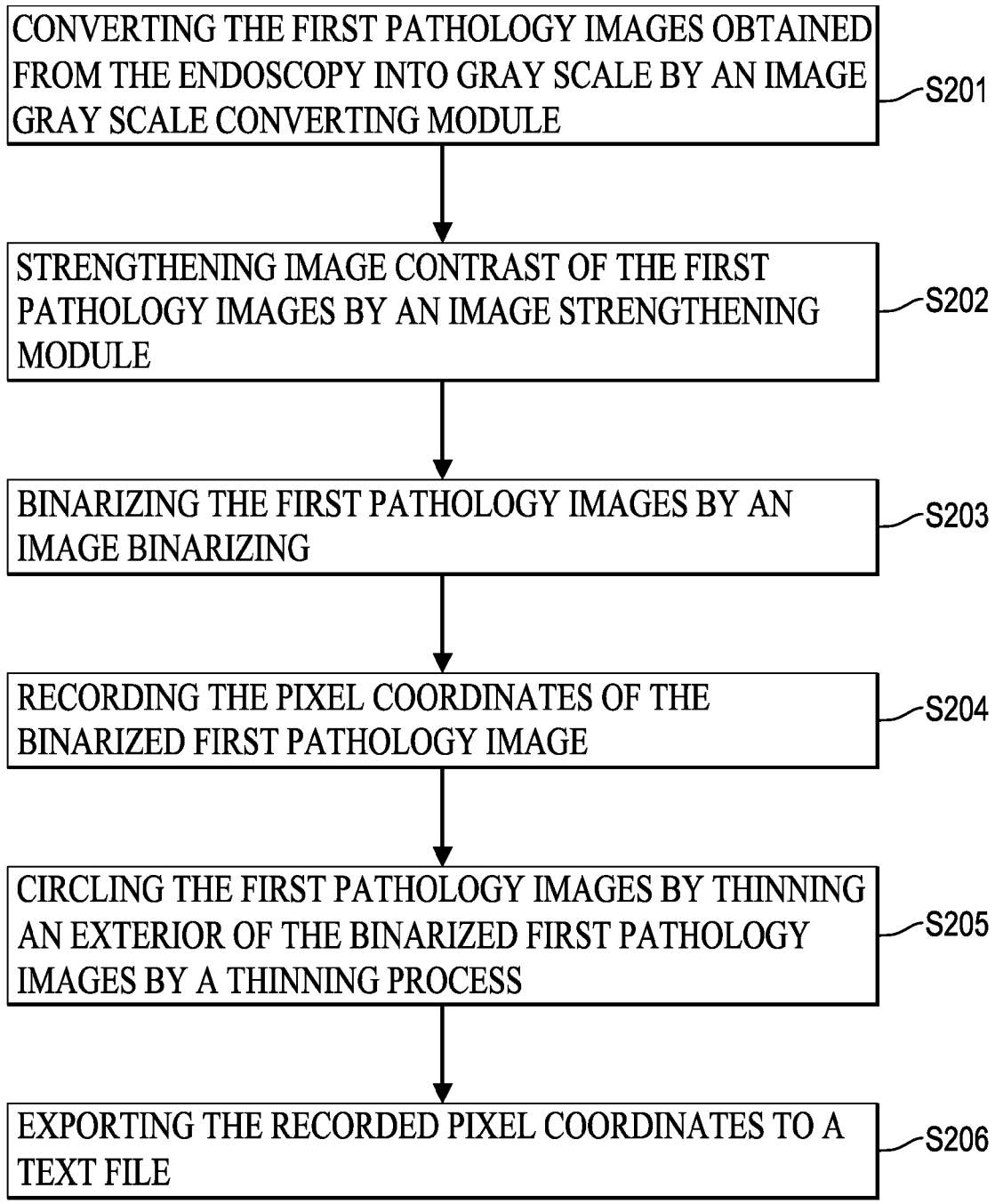
FIG. 4 is a flow chart of steps to process images via an image process module in the present invention.

FIG. 4 is a flow chart of the image processing steps for the image processing module in the present invention. As shown in FIG. 4, in order to automatically circle IPCL area and record the pixel coordinates of the first pathology images, in step S201, the first pathology images obtained from the endoscopy are converted into gray scale by a gray scale image converting module. Gray scale of the first pathology images can be obtained by a computer with image processing function. Thereafter, in step S202, an image strengthening module is used to strengthen image contrast of the gray scale of the first pathology images. The strength of the image contrast can also be obtained by the computer with image processing function. Then, in step S203, after strengthening the contrast of the gray scale of the first pathology images, an image binarizing module is used to binarize the first pathology images. The image binarizing module is made by the program design software in the computer to binarize the first pathology images. In step S204, the pixel coordinates of the binarized first pathology images are recorded. Then, in step S205, by a thinning process, the first pathology images may be circled by thinning an exterior of the binarized first pathology images. In step S206, the recorded pixel coordinates are exported to a text file. The computer with hyper-spectral imaging technique software reads the lesion images again and reads the pixel coordinates in the text file at the same time.

By the aforementioned steps, the first pathology images are converted by the hyper-spectral imaging technique and the stimulation spectra of the first pathology images is obtained. The aforementioned image processing steps, such as gray scale processing, image contrast strengthening, image thinning processing and image reading, and so on, can be performed by an image processing module in the present invention. The image processing module performs the image processing by the image processing application software via the computer. The image processing is well known by the person having ordinary skill in the art, and the detailed description thereof is omitted herein.

The average reflective spectra of the lesions at the white light, iodine staining or NBI endoscopy are obtained by the hyper-spectral imaging technique. The images at the white light and Lugol's chromoendoscopy are sampled by 400 (20×20) pixels. The first pathology images at the NBI endoscopy directly and automatically circle the IPCL types. Therefore, the number of the sampled pixels is larger and one thousand coordinates are sampled during the experiment period and one thousand reflective spectra may be obtained.

Figure 5:
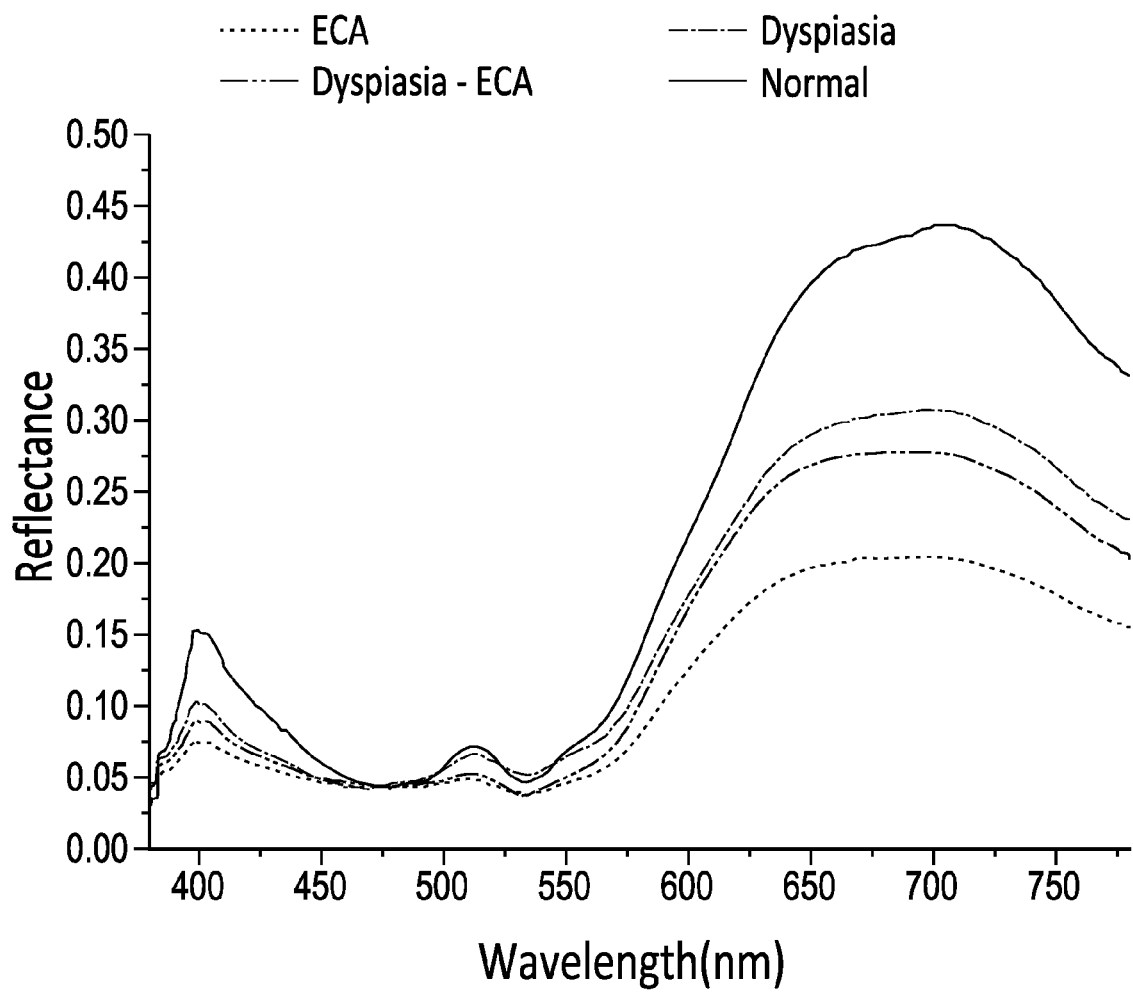
FIG. 5, FIG. 6, and FIG. 7 are waveform diagrams of an average result of reflective spectra.
Figure 6:
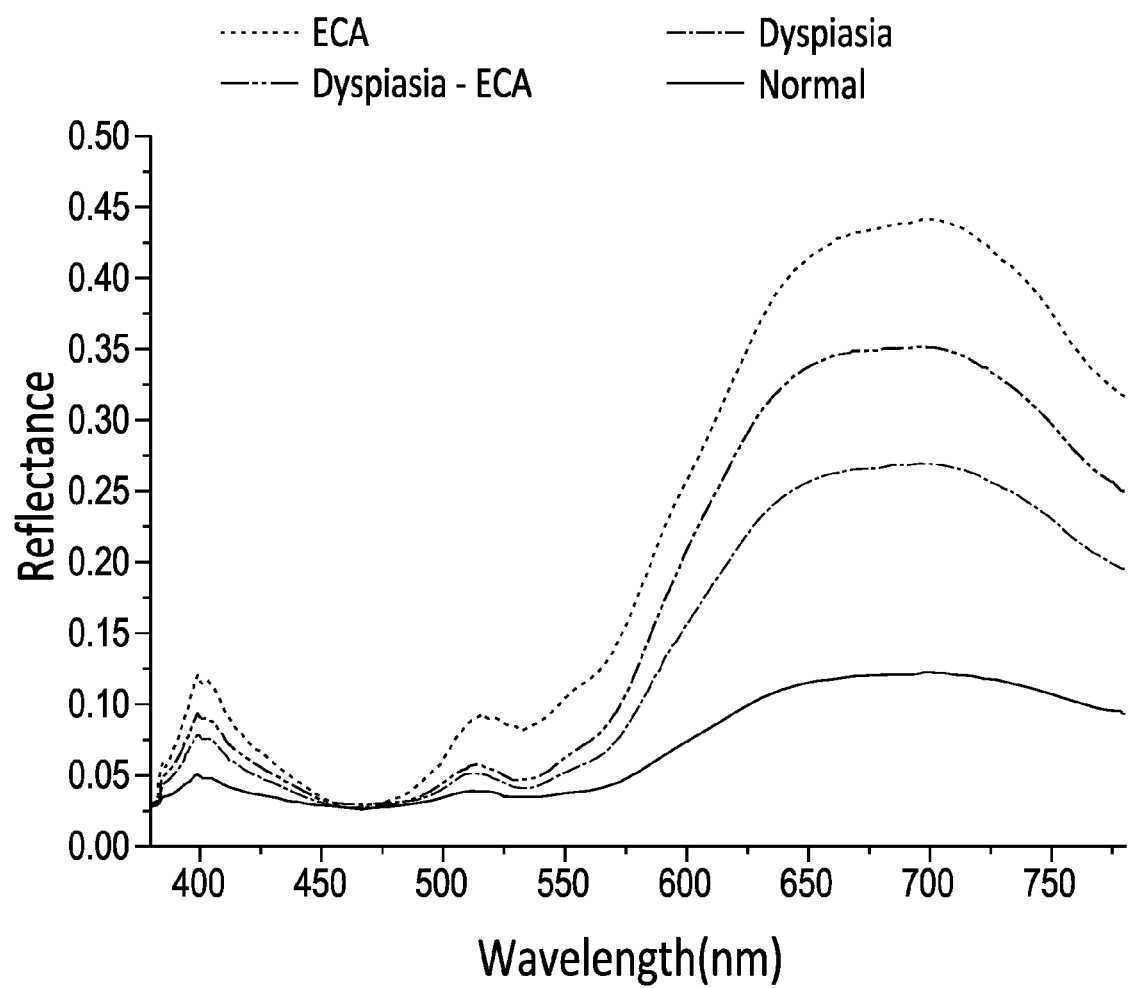
Figure 7:
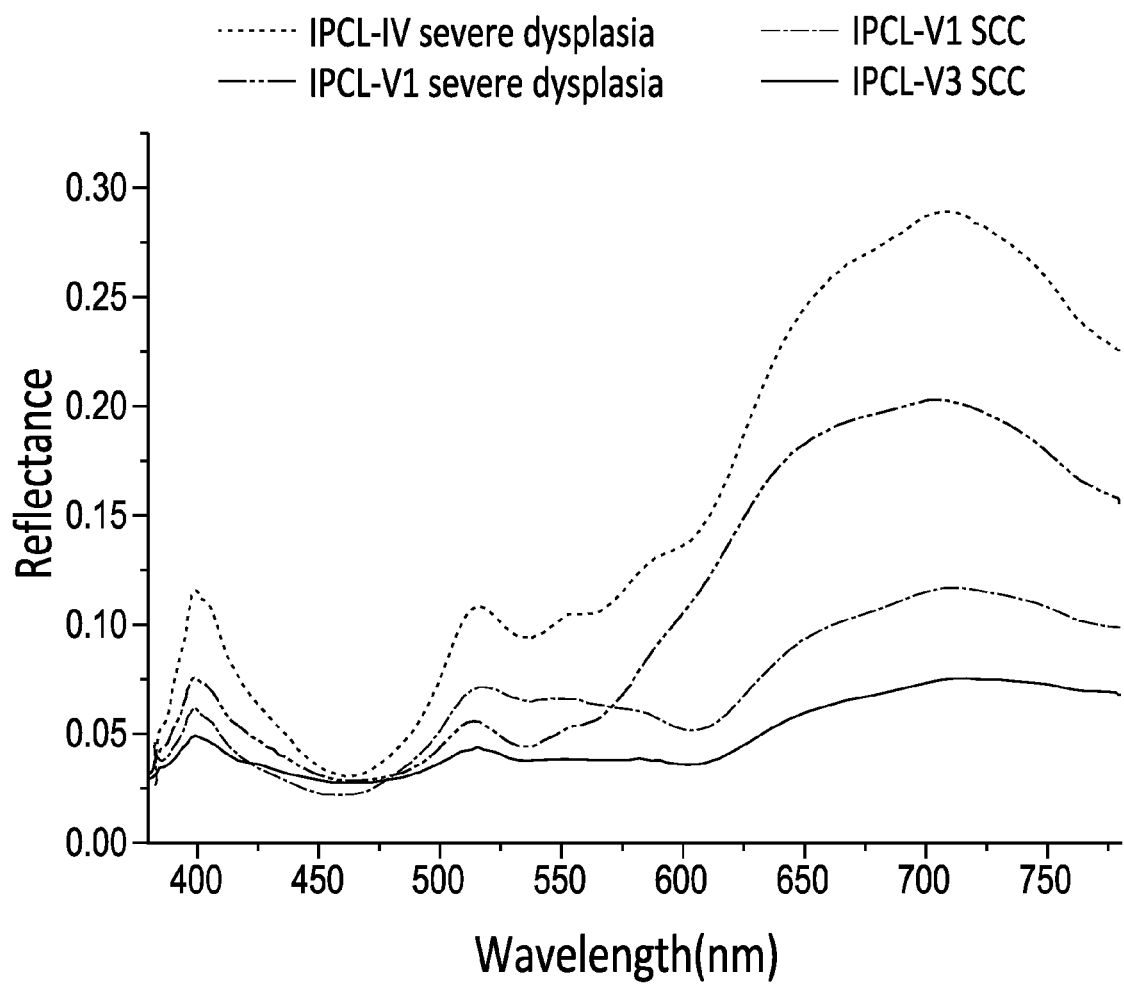
Figure 8:
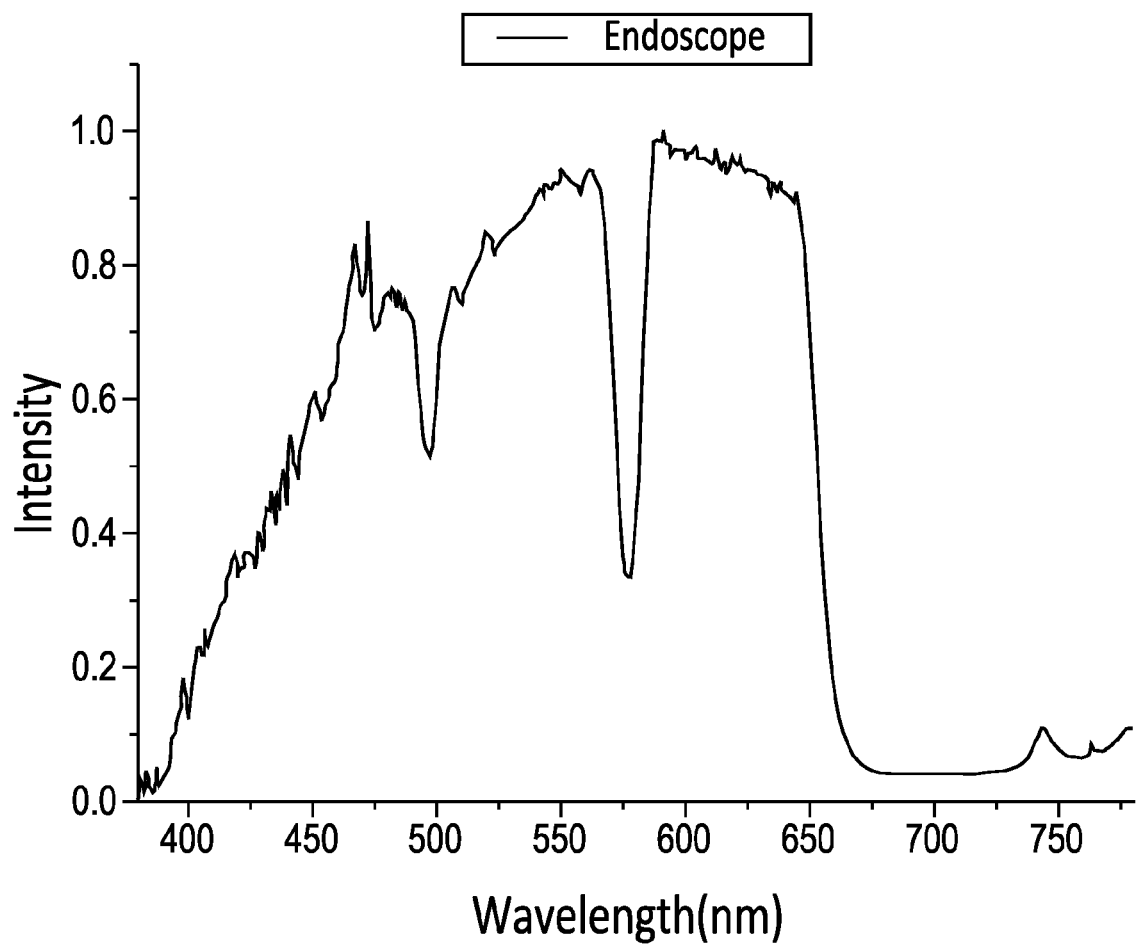
FIG. 8 is a spectrum diagram of a light source of an endoscopy.

In view of the difference of the reflective spectra in FIG. 5, the reflective spectra are gradually decreased in accordance with the degree of the lesions (normal, precancerous lesions or cancerous lesions). Generally, the color of the normal esophageal mucosa is whiter than the stomach mucosa. When the precancerous lesions and the cancerous lesions occur, the surface of the esophageal mucosa may include concavities or bulges generated by the lesions and have uneven flatness. The lesions on the mucosa are more darkly red than the surrounding mucosa. Therefore, if the lesions are more severe, the reflective rate of the spectra is lower. In addition, the corresponding reflective rates of the wave band of the blue light and the green light are lower than the wave band of the red light. Since the occurrence of the esophageal cancer will have angiogenesis within the mucosa to provide extra nutrition and oxygen for the cancerous cells and the absorbing rate of the extra heloglobin is greater than the green light and blue light, a drop is found in the reflective rate for the wavelength 530 nm. In addition, a peak respectively occurs at the wavelengths 410 nm and 520 nm and the result requires analyzing more pertinent documents to make sure the occurrence reason. On the contrary, the difference of the reflective spectra of the image in the Lugol's chromoendoscopy is shown in FIG. 6, and the difference of the spectra is gradually increased in accordance with the sequence of the normal, precancerous lesions and cancerous lesions. Since the normal esophageal mucosa is squamous cells, the iodine solution is reacted with glycogen within the cells to stain the mucosa brown. When the cancerous cells occupy the epithelium to cause the decreasing and disappearing of the glycogen, the iodine solution may not stain the mucosa brown. The probabilities of the occurrence of the cancerous lesions at the unstained area of the mucosa are extremely high. The area is whiter than the surrounding mucosa in accordance with the severity of the lesions. The tendency of the reflective spectra of the image in the NBI endoscopy is shown in FIG. 7 and the difference thereof shows more expanded, twisted, irregular patterns in accordance with the IPCL to cause the reflective rate of the spectra to gradually decrease. The average reflective spectra in the three aforementioned endoscopy images are not affected because of the light source of the endoscopy. The light source spectra of the endoscopy are showed in FIG. 8.

Figure 9:
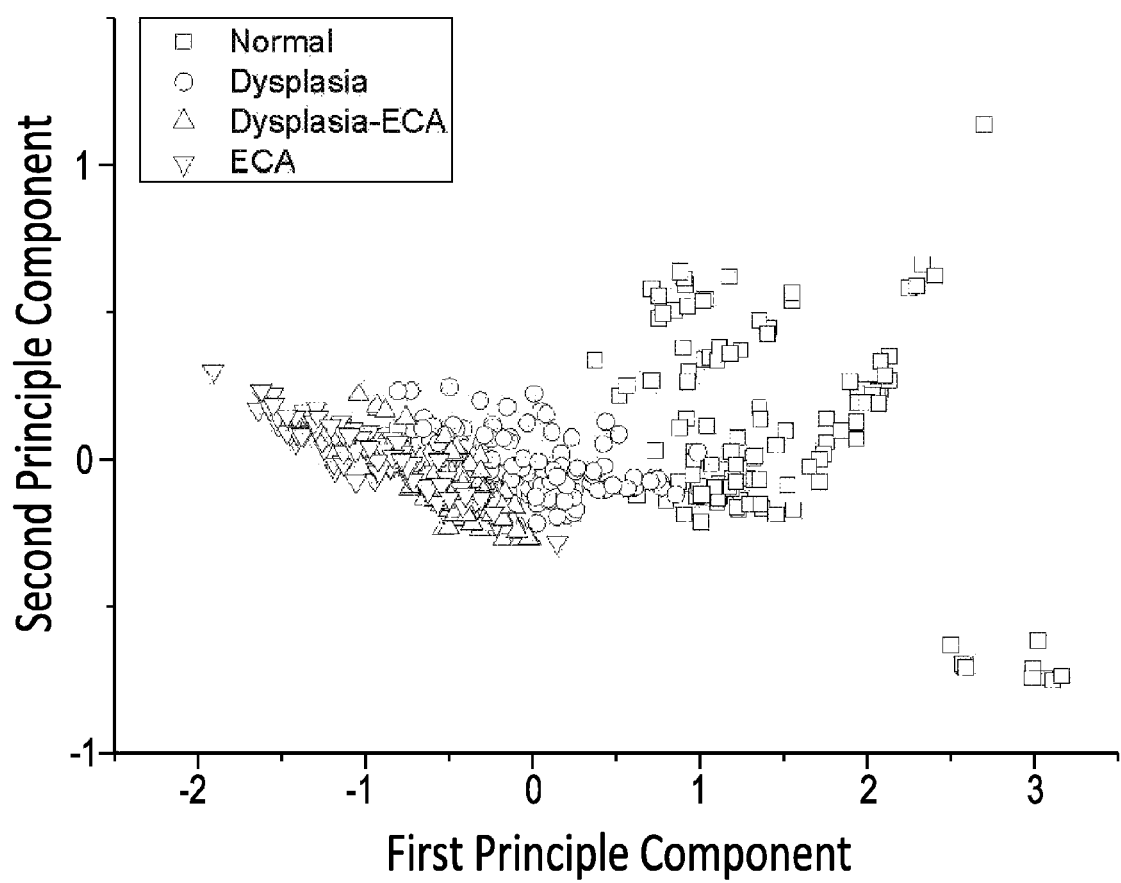
FIG. 9, FIG. 10, and FIG. 11 are principle component score diagrams.
Figure 10:
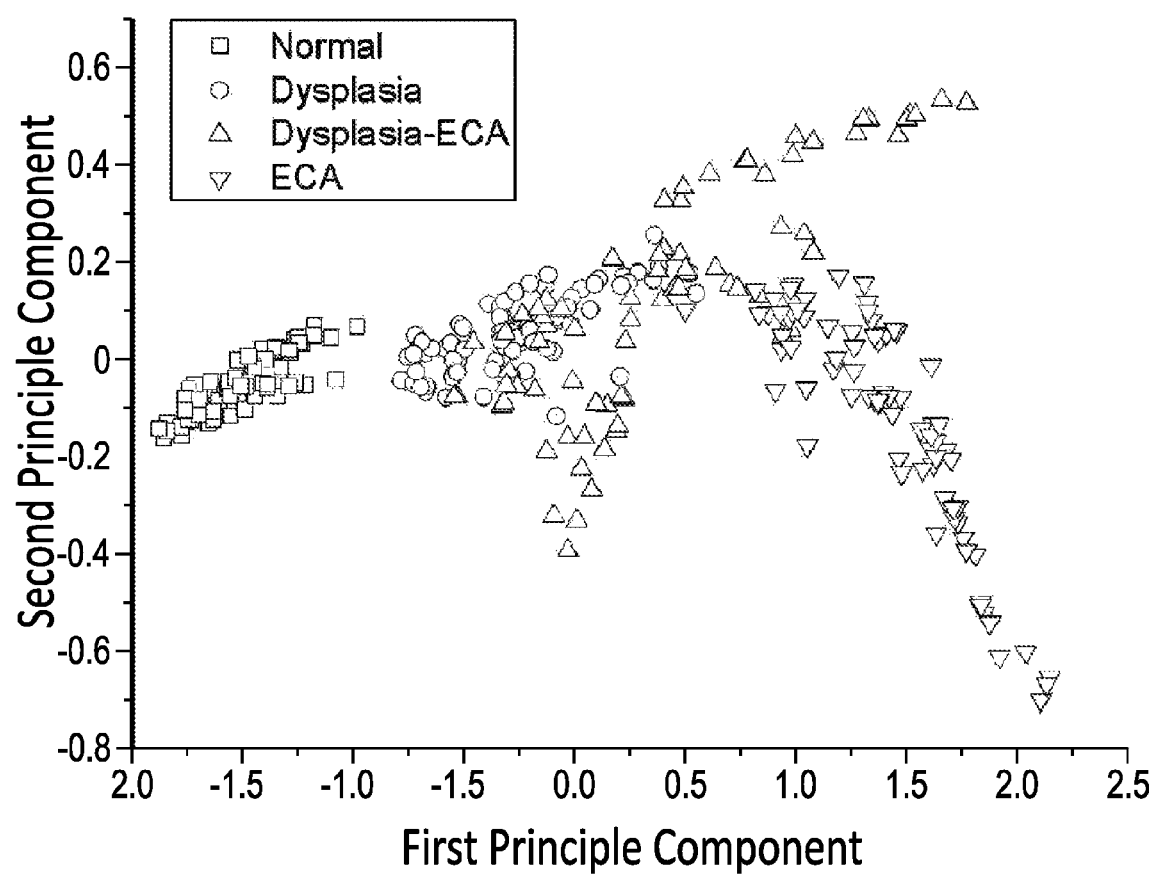
Figure 11:
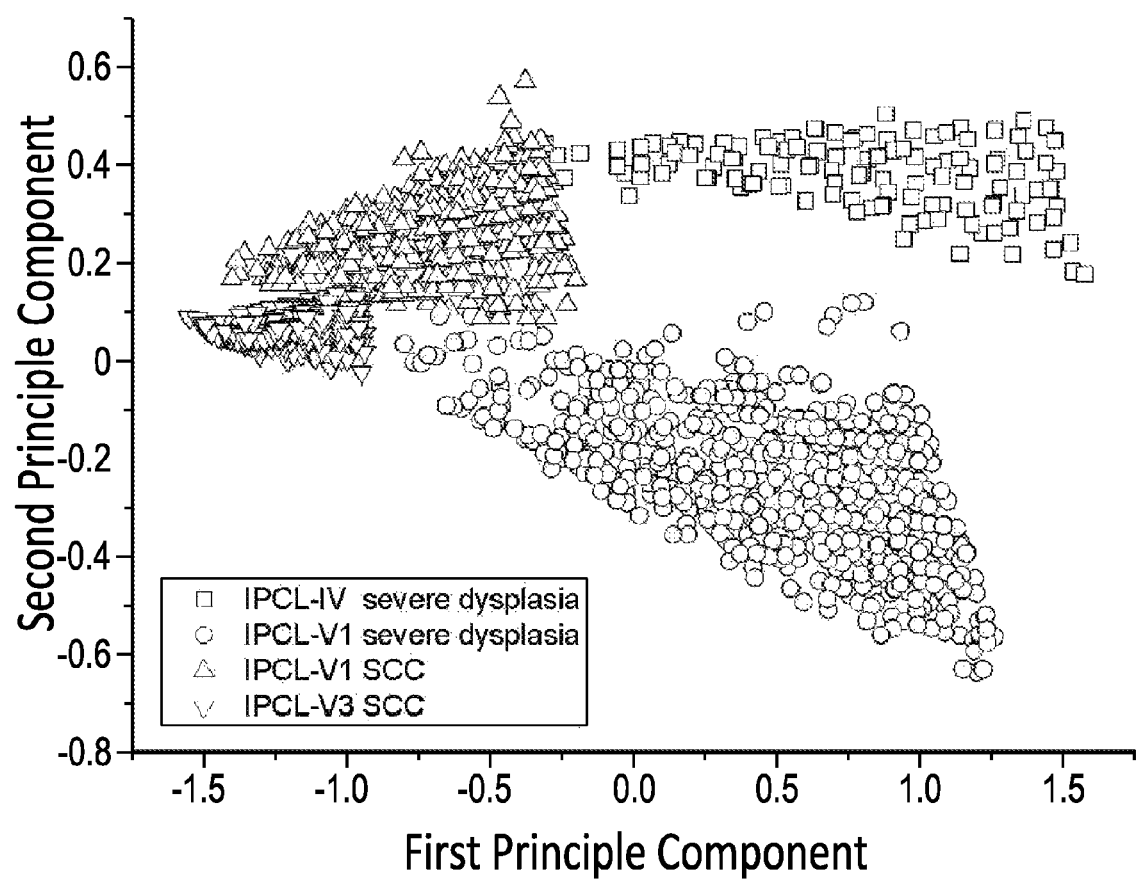

The characteristics of the spectra for the white light, iodine staining and NBI endoscopy may be obtained by the principle component analysis and the principle component score diagrams in FIG. 9, FIG. 10 and FIG. 11 are drawn by a software called Original in accordance with the first principle components and the second principle components. FIG. 9 shows a result of the spectra characteristics of the images in the white light endoscopy. The positions of the ECA are located between −1.9 and 0.25 of the first principle component (FPC) and between −0.35 and 0.35 of the second principle component (SPC). The range of the dysplasia-ECA is about −0.90<FPC<0.05 and −0.30<SPC<0.30. The range of the dysplasia is about −0.75<FPC<1.00 and −0.20<SPC<0.35. The range of the normal is about 0.30<FPC<3.25 and −0.75<SPC<1.25. The overlapping areas among the dysplasia, dysplasia-ECA and cancer are deemed to be gray areas. The spectra characteristics of the endoscopy images of the normal esophageal mucosa tend to disperse. Substantially, the differences of the normal esophageal mucosa and the cancerous lesions are readable and include a tendency from right to left. The spectra characteristics of the images in the Lugol's chromoendoscopy are shown in FIG. 10. The range of the normal is about −1.90<FPC<−0.90 and −0.19<SPC<0.10. The range of the dysplasia is about 0.80<FPC<0.50 and −0.16<SPC<0.28. The range of the dysplasia-ECA is about 0.40<FPC<1.70 and −0.42<SPC<0.56. The range of ECA is about 0.00<FPC<2.20 and −0.74<SPC<0.18. Similarly, the gray areas among the dysplasia, the dysplasia-ECA and ECA also exist. The endoscopy images of the esophageal mucosa in dysplasia-ECA and ECA trend to disperse. Substantially, the differences of the spectra characteristics are readable. On the contrary, the tendency is from left to right in accordance with the normal esophageal mucosa to the cancerous lesion. The spectra characteristics of the images in the NBI endoscopy are shown in FIG. 11. The range of the IPCL-V3 SCC is about −1.70<FPC<−0.90 and −0.15<SPC<0.02. The range of IPCL-V1 SCC is about 1.40<FPC<−0.30 and −0.02<SPC<0.40. The range of IPCL-IV severe dysplasia is about 1.40<FPC<−0.30 and −0.02<SPC<0.40. The range of IPCL-IV severe dysplasia is about −0.60<FPC<1.60 and 0.05<SPC<0.31. The gray area formed by the four spectra characteristics is smaller. The characteristics of the IPCL type tend to restrain.

With reference to FIG. 1, the cancerous lesion identifying method by the hyper-spectral imaging technique can evaluate the probabilities of the occurrence of cancerous lesions in the patients at each of the stages in accordance with the pixel coordinates after image processing and the principle component analysis. In the step S103 of the cancerous lesion identifying method by the hyper-spectral imaging technique of the present invention, a plurality of triangle areas are defined in the principle component score diagram. In step S104, it is to determine whether a principle component score in a second stimulating spectrum of a second pathology image is located within one of the triangle areas or not.

The principle component is recognized from the perspective of ease of observation of the data, so the characteristics in each of the data can be seen clearly. Each of the sample values seen in the principle component is called principle component score. The equation of the principle component score is as the following:

$$y_j = a_{j1}(x_{1i} - \bar{x}_1) + a_{j2}(x_{2i} - \bar{x}_2) + \ldots + a_{jn}(x_{ni} - \bar{x}_n) \quad (17)$$

Where $x_{1i}, x_{2i}, \ldots, x_{ni}$ are the corresponding spectrum strength values for the first, second to nth wavelengths respectively and $\bar{x}_{1i}, \bar{x}_{2i}, \ldots, \bar{x}_{ni}$ are the average spectrum strength values for the first, second to nth wavelengths respectively. Those parameters $a_{j1}, a_{j2}, \ldots, a_{jn}$ are the parameters of the characteristic vector after the spectra are calculated in the covariance matrix. In accordance with the theory basis of the principle component analysis, the first principle component (y1) occupies most data in the original data and is deemed to be a comprehensive index. The second principle component (y2) occupies a portion of the data and is used for classification of the groups. Therefore, by the stimulating spectra obtained by the image processing stated in the aforementioned chapters, the principle component analysis is applied to generate the principle component score diagram to observe the tendency of the spectra characteristics of the lesion images.

Figure 12:
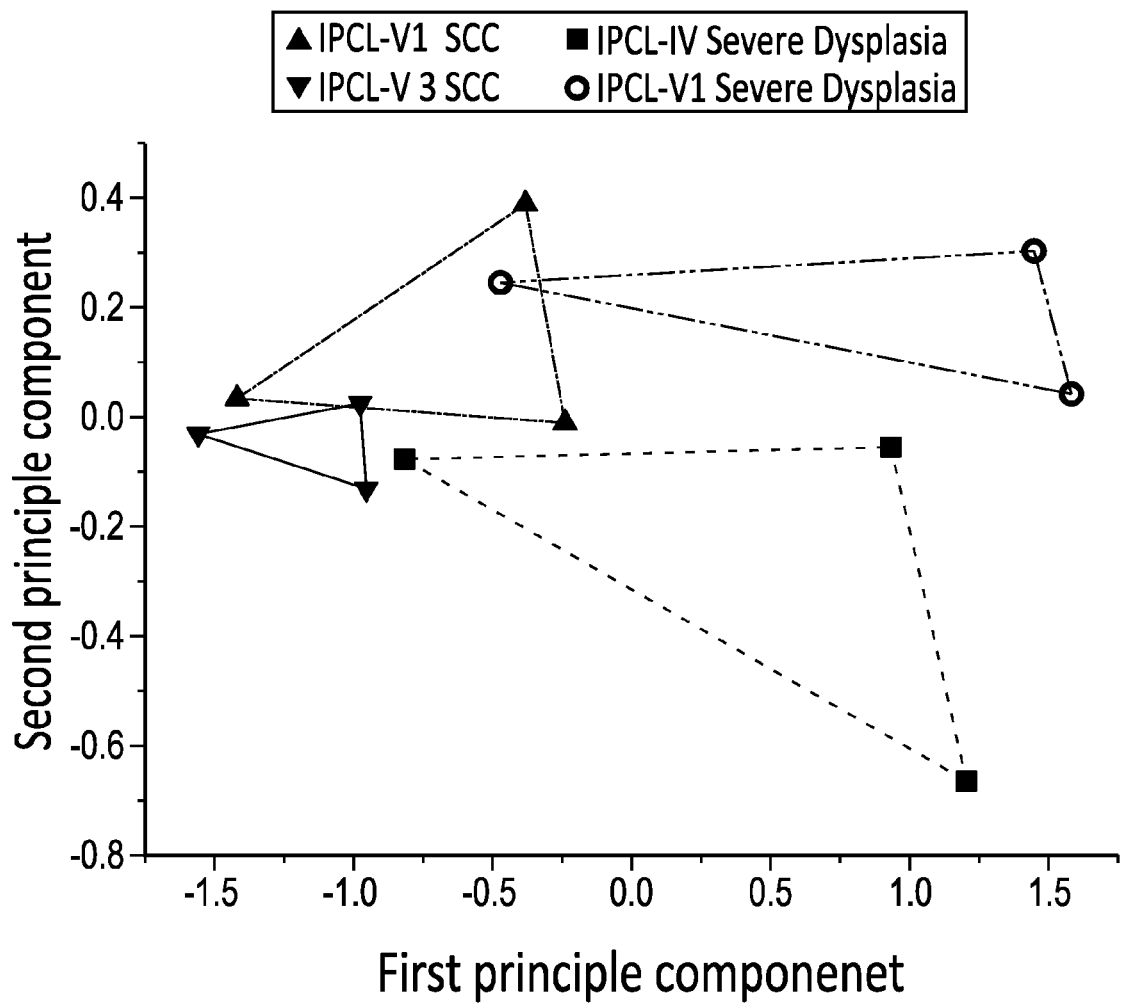
FIG. 12 is a diagram of defining triangle areas in the principle component analysis.
Figure 13:
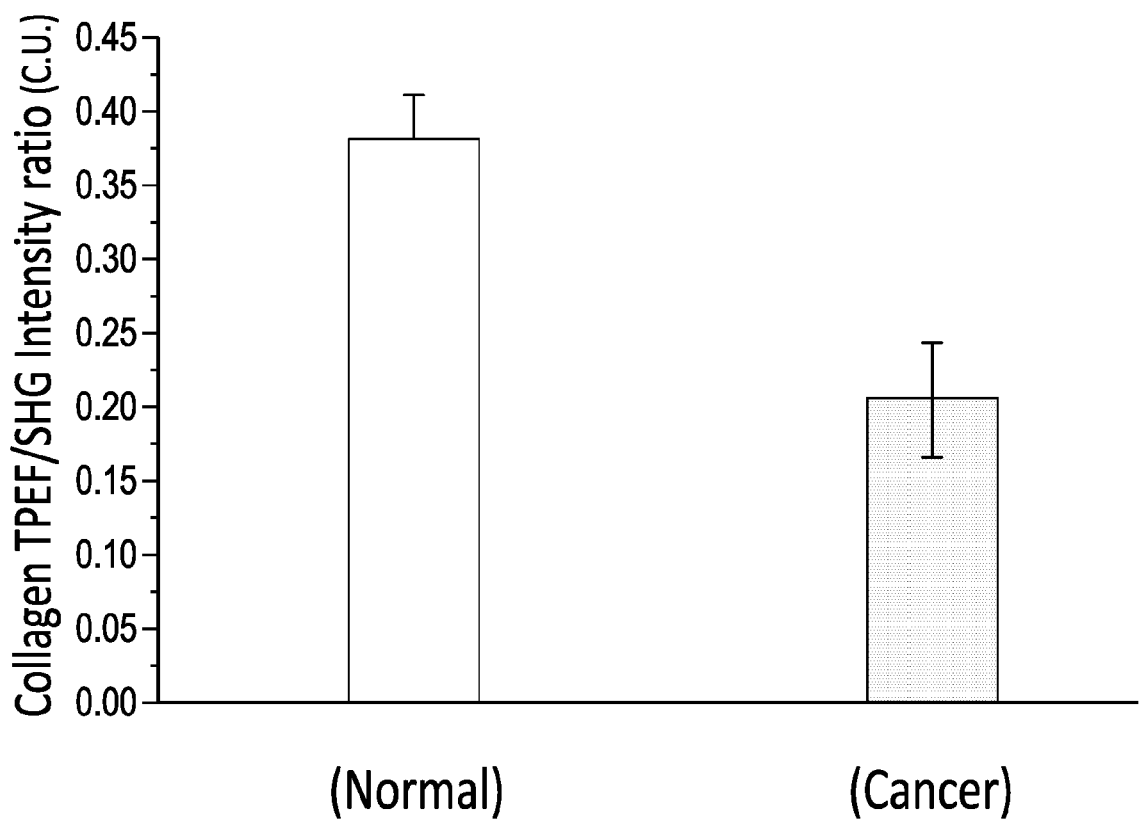
FIG. 13 is a comparison diagram of signal strength ratio between SHG and TIPEF of the normal tissues and cancerous lesions of the esophagus.
Figure 14:
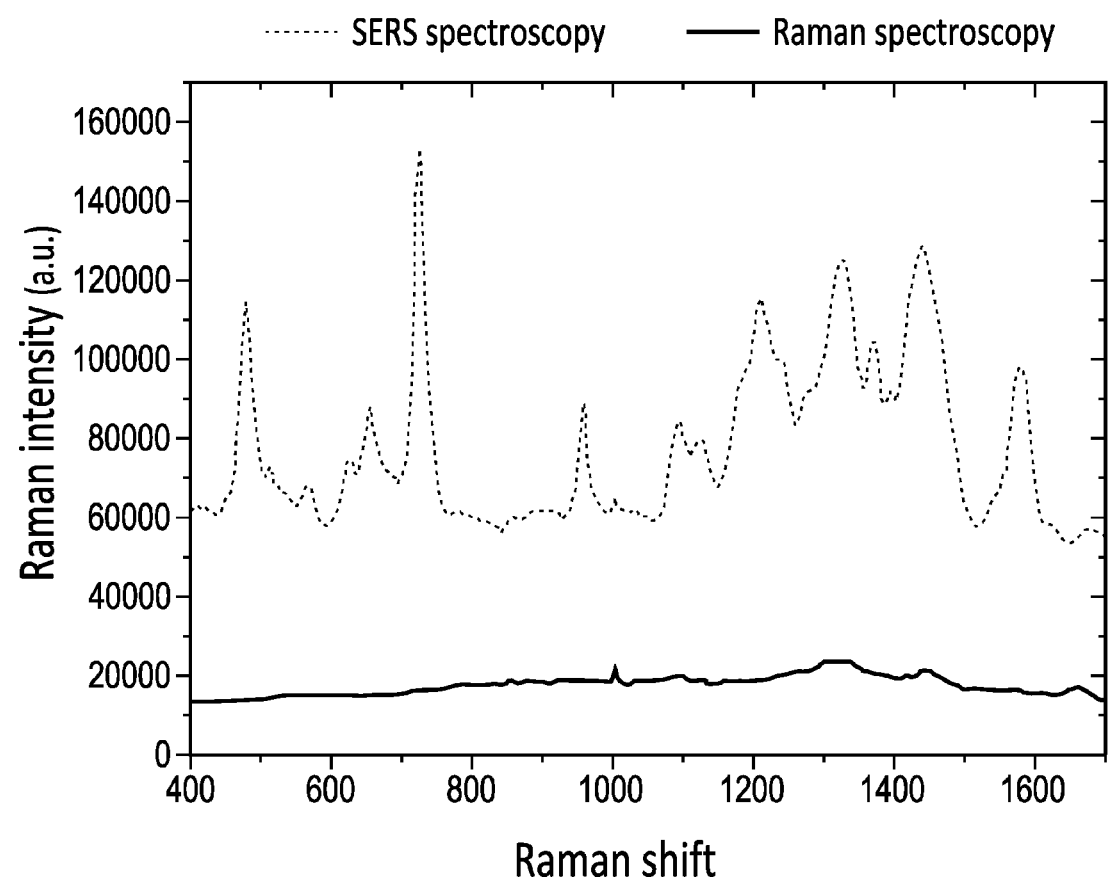
FIG. 14 is a comparison diagram of Raman signal strength of esophageal tissues with or without dropping of silver nano particles.
Figure 15:
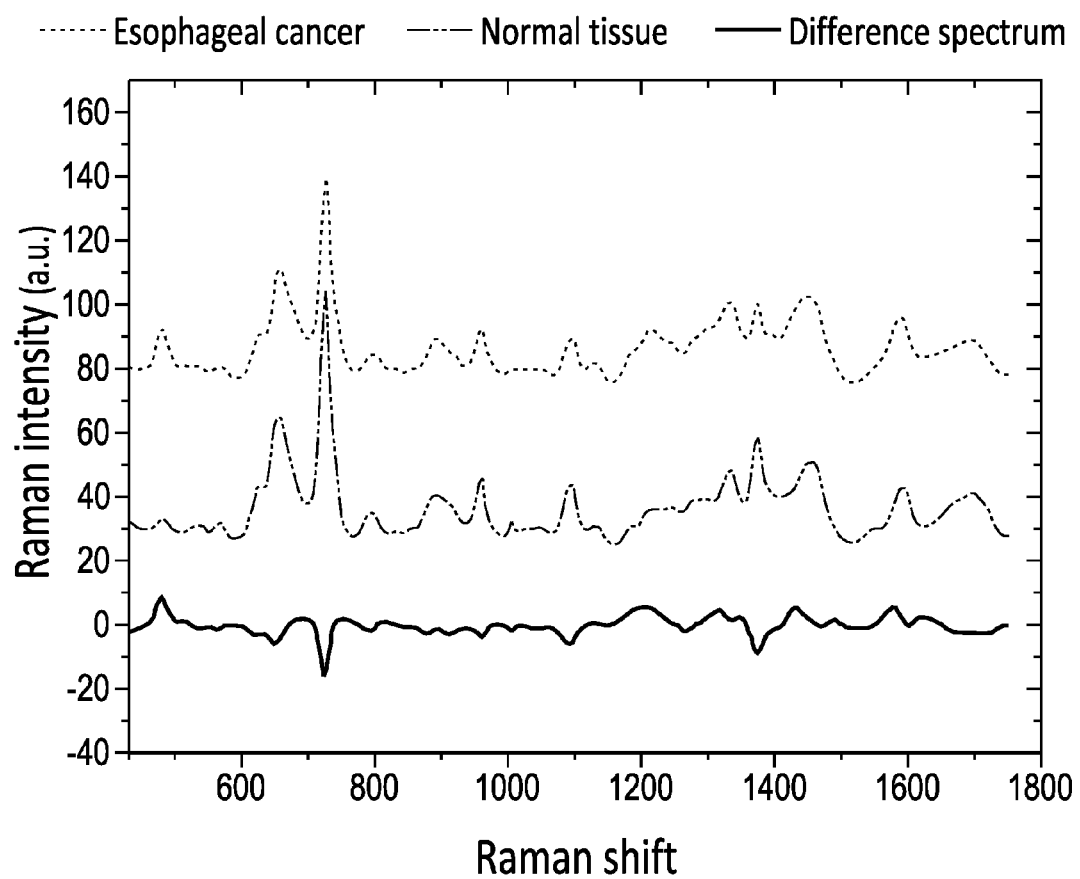
FIG. 15 is a comparison diagram of Raman average spectra between the normal esophageal tissues or cancerous tissues.
Figure 16:
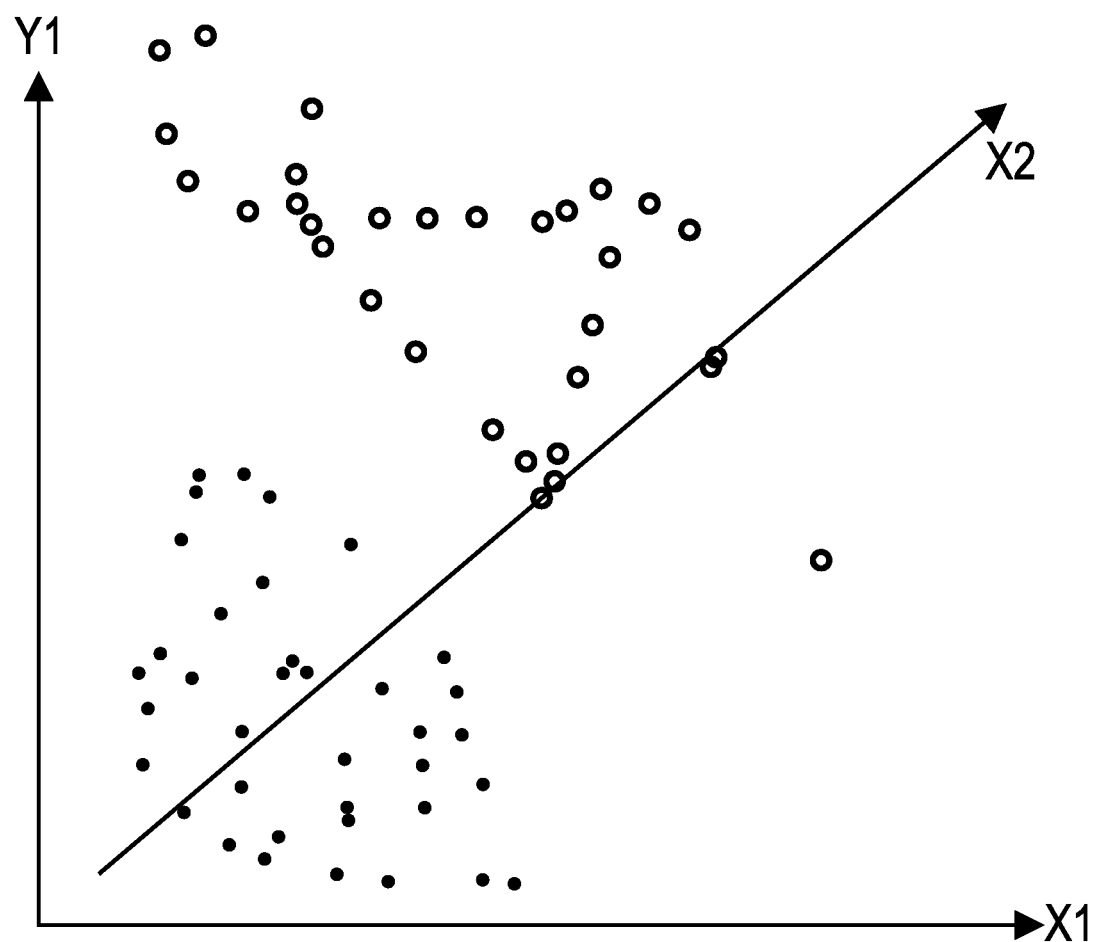
FIG. 16 is a diagram of a spindle of the principle component analysis.

In order to evaluate the cancerous stages occurring to the patients, the principle component score of the stimulating spectra of the image in the endoscopy for the patient is determined to be located with the triangle areas or not, which can be determined by the detection method of the triangle areas. As shown in FIG. 12, the image spectra obtained in the endoscopy by stimulating and analyzing of the hyper-spectral imaging system are applied in the principle component score diagram. The obtained average stimulating spectra are classified and the triangle area is defined to be the maximum area of the triangle in the principle component score diagram generated by the principle component analysis of the aforementioned triangle area. For example, one point at the left hand side in the x axis is selected to be a reference point and two other points are randomly selected. The area of those three points are calculated by the computer and then two other points are selected to calculate another triangle area and the two triangle areas are compared to find the larger triangle area. In accordance with the comparison method of the triangle area and the computer calculation, the triangle with maximum area can be quickly found in the principle component score diagram and the three coordinates of the three points for the triangle with maximum area may also be found. When the three coordinates for the triangle area are found, the coordinates of the vector AB and AC can also be found. For example, the three coordinates of the triangle area are A (a1, a2), B (b1, b2) and C (c1, c2) and the vector AB=(b1−a1, b2−a2), vector AC=(c1−a1, c2−a2). And the area of $\triangle ABC$ is:

$$\triangle ABC = 1/2 \left\| \begin{matrix} b1-a1 & c1-a1 \\ b2-b2 & c2-a2 \end{matrix} \right\| \quad (18)$$

In accordance with the area of the $\triangle ABC$, if one X point is given and the coordinate thereof is X(s, t), the areas of $\triangle XAB$, $\triangle XBC$, and $\triangle XAC$ can be calculated. If the X point is located outside of the $\triangle ABC$, the following condition will be satisfied:

$$\triangle XAB + \triangle XBC + \triangle XAC > \triangle ABC \quad (19)$$

If the X point is located on the edge of or outside of the $\triangle ABC$, the following condition will be satisfied:

$$\triangle XAB + \triangle XBC + \triangle XAC = \triangle ABC \quad (20)$$

According to the determination method of the triangle area, whether the principle component score of the stimulating spectra of the image in the endoscope for the patient is located within one of the aforementioned and defined triangle areas, such as the area of the IPCL-IV severe dysplasia, IPCL-V1 severe dysplasia, IPCL-V1 SCC and IPCL-V3 SCC, may be known.

Finally, in the step S105, when the principle component score of the second stimulating spectrum is located within one of the triangle areas, the second pathology image is confirmed to belong to one cancerous lesion image. The detection for four different cancerous lesions is shown in the following.

The principle component score is set to be a testing point. If the testing point is located within the triangle area, the lesion image for the testing point belongs to the stage of cancerous lesion. For example, the esophageal cancer with 1 to 4 stages:

1. IPCL-V3 SCC: U is the testing point. If the following condition is satisfied ($\Delta UDE+\Delta UEF+\Delta UDF=\Delta DEF$), the patient belongs to this cancerous lesion stage.

2. IPCL-V1 SCC: U is the testing point. If the following condition is satisfied ($\Delta UDE+\Delta UEF+\Delta UDF=\Delta DEF$), the patient belongs to this cancerous lesion stage.

3. IPCL-V1 V1 severe dysplasia: U is the testing point. If the following condition is satisfied ($\Delta UDE+\Delta UEF+\Delta UDF=\Delta DEF$), the patient belongs to this cancerous lesion stage.

4. IPCL-IV severe dysplasia: U is the testing point. If the following condition is satisfied ($\Delta UDE+\Delta UEF+\Delta UDF=\Delta DEF$), the patient belongs to this cancerous lesion stage.

5. If the testing point of U does not satisfy the aforementioned condition, U cannot be detected.

According to the cancerous lesion identifying method by hyper-spectral imaging technique, the cancerous lesion image is digitized and the principle component analysis is used to quickly evaluate the probability of the occurrence of the cancer at each of the stages for the patient. The diagnosis of the doctor is effective and fast to help the patient to have early stage treatment.

What is claimed is:

1. A cancerous lesion identifying method via hyper-spectral imaging technique, comprising steps of:
   acquiring a plurality of first pathology images via an endoscopy, wherein the first pathology images are cancerous lesion images respectively;
   importing the first pathology images into an image processing module to acquire a plurality of first simulating spectra of the first pathology images so as to generate a principle component score diagram in accordance with the first simulating spectra;
   defining a plurality of triangle areas in the principle component score diagram in accordance with the first simulating spectra;
   determining whether a principle component score of a second simulating spectrum of a second pathology image is within any one of the triangle areas; and
   confirming the second pathology image belongs to one of the cancerous lesion images when the principle component score of the second simulating spectrum is within any one of the triangle areas.

2. The cancerous lesion identifying method as claimed in claim 1, wherein the first pathology images and the second pathology image are imported into a hyper-spectral imaging system to obtain the first simulating spectra and the second simulating spectrum.

3. The cancerous lesion identifying method as claimed in claim 1, wherein the step of defining the triangle areas in the principle component score diagram in accordance with the first simulating spectra includes steps of:
   converting the first pathology images to be gray scale via a gray scale image converting module;
   enhancing contrast of the first pathology images via an image enhancing module;
   binarizing the gray scale of the first pathology images via an image binarizating module;
   recording a plurality of pixel coordinates of the first pathology images after binarization; and
   generating the principle component score diagram by exporting the pixel coordinates of the recorded first pathology images.

4. The cancerous lesion identifying method as claimed in claim 1, wherein the step of defining the triangle areas in the principle component score diagram in accordance with the first simulating spectra is to implement a principle component analysis method to generate the principle component score diagram.

5. The cancerous lesion identifying method as claimed in claim 1, wherein the principle component score is a test point located within one of the triangle areas, and the second pathology image is determined to be a precancerous lesion corresponding to one of the triangle areas when the test point is located within one of the triangle areas.

6. The cancerous lesion identifying method as claimed in claim 1, wherein the first pathology images are a plurality of esophageal lesion images.

7. The cancerous lesion identifying method as claimed in claim 1, wherein the first pathology images and the second pathology image are epidermis intravascular images.

8. The cancerous lesion identifying method as claimed in claim 1, wherein the triangle areas are maximum triangle areas in the principle component score diagram.

\* \* \* \* \*